United States Patent
Yang et al.

(10) Patent No.: US 11,254,635 B2
(45) Date of Patent: Feb. 22, 2022

(54) EMODIN SUCCINYL ESTER COMPOUND, PREPARATION METHOD THEREFOR AND APPLICATION THEREOF

(71) Applicant: JIANGSU KANION PHARMACEUTICAL CO., LTD., Lianyungang (CN)

(72) Inventors: Baofeng Yang, Lianyungang (CN); Wei Xiao, Lianyungang (CN); Yong Zhang, Lianyungang (CN); Zhimin Du, Lianyungang (CN); Jinhui Wang, Lianyungang (CN); Zhenzhong Wang, Lianyungang (CN); Yunlong Bai, Lianyungang (CN); Yanjie Lv, Lianyungang (CN); Xueshi Huang, Lianyungang (CN); Chaoqian Xu, Lianyungang (CN); Xin Li, Lianyungang (CN)

(73) Assignee: JIANGSU KANION PHARMACEUTICAL CO., LTD., Lianyungang (CN)

( * ) Notice: Subject to any disclaimer, the term of this patent is extended or adjusted under 35 U.S.C. 154(b) by 0 days.

(21) Appl. No.: 16/767,909

(22) PCT Filed: Nov. 30, 2018

(86) PCT No.: PCT/CN2018/118698
§ 371 (c)(1),
(2) Date: May 28, 2020

(87) PCT Pub. No.: WO2019/109873
PCT Pub. Date: Jun. 13, 2019

(65) Prior Publication Data
US 2020/0399199 A1    Dec. 24, 2020

(30) Foreign Application Priority Data

Dec. 7, 2017  (CN) .......................... 201711288330.5
Dec. 7, 2017  (CN) .......................... 201711290937.7

(51) Int. Cl.
| | | |
|---|---|---|
| *C07C 67/08* | (2006.01) | |
| *A61P 3/06* | (2006.01) | |
| *C07C 67/14* | (2006.01) | |
| *C07C 67/56* | (2006.01) | |
| *A61K 47/44* | (2017.01) | |
| *C07C 69/017* | (2006.01) | |
| *C07C 69/40* | (2006.01) | |
| *C07C 69/675* | (2006.01) | |

(52) U.S. Cl.
CPC .............. *C07C 67/08* (2013.01); *A61P 3/06* (2018.01); *C07C 67/14* (2013.01); *C07C 67/56* (2013.01); *A61K 47/44* (2013.01); *C07C 69/017* (2013.01); *C07C 69/40* (2013.01); *C07C 69/675* (2013.01); *C07C 2603/22* (2017.05)

(58) Field of Classification Search
CPC ......... C07C 67/08; C07C 69/40; C07C 67/14; C07C 67/56; C07C 67/30; C07C 69/675; C07C 2603/22; C07C 69/67; C07C 2603/24; C07C 69/017; A61K 31/225; A61K 47/44; A61K 9/00; A61K 9/0014; A61P 17/02; A61P 3/06; A61P 3/10
See application file for complete search history.

(56) References Cited

U.S. PATENT DOCUMENTS 7,268,162 B2 * 9/2007 Palu .................... C07C 69/40
514/510

FOREIGN PATENT DOCUMENTS

| CN | 102363044 A | 2/2012 |
|---|---|---|
| CN | 105663099 | 6/2016 |
| CN | 108047046 | 5/2018 |
| CN | 108186623 | 6/2018 |
| CN | 108245502 | * 7/2018 |

OTHER PUBLICATIONS

CN108245502 translation (Year: 2018).*
Vranic (Basic Princviples of Drug-Excipients Interactions, Bosnian Journal of Basic Medical Sciences, 4 (2), pp. 56-58, Published 2004) (Year: 2004).*
Liang et al., "Synthesis of 1,8-dihydroxy-3-acetyl-6-methyl-9,10 anthraquinone and its inhibition effect on ovarian carcinoma cells SKOV3", Chinese Journal of New Drugs, 2012, 21(9).

(Continued)

*Primary Examiner* — Yevgeny Valenrod
*Assistant Examiner* — Blaine G Doletski
(74) *Attorney, Agent, or Firm* — Maier & Maier, PLLC

(57) ABSTRACT

Disclosed in the present invention are an emodin succinyl ester compound, a preparation method therefor and a use thereof, the emodin succinyl ester compound having the structure as represented by formula I (R being a $C_{1-5}$ alkyl group). The method provided in the present invention has a simple method course, and may effectively save time in synthesis and reduce costs, being simple to operate, being easy to implement, and being suitable for industrial production. Experiments show that the emodin succinyl ester compound of the present invention may better promote the healing of diabetic wounds than emodin, and may be used for preparing a drug for promoting the healing of diabetic wounds. Moreover, it has been confirmed by means of performing pharmacological experiments on rats suffering from experimentally mixed hyperlipidemia that the emodin succinyl ester compound of the present invention is superior to emodin, and has the advantages of having a remarkable blood fat lowering effect, being safe, being simple and convenient to administer, the raw materials being low cost and readily available, and being easy to transport and store.

15 Claims, 5 Drawing Sheets

(56) References Cited

OTHER PUBLICATIONS

Chen et al. "Emodin Ameliorates High Glucose Induced-Podocyte Epithelial-Mesenchymal Transition In-Vitro and In-Vivo " Cellular Physiology and Biochemistry vol. 35, No. 4. Jan. 1, 2015. pp. 1425-1436.

Narender et al. "Apoptosis and DNA intercalating activities of novel emodin derivatives." RSC Advances, The Royal Society of Chemistry. 2013. 9 pages.

Narender et al. "Preparation of novel antiproliferative emodin derivatives and studies on their cell cycle arrest, caspase dependent apoptosis and DNA binding interaction." Phytomedicine. vol. 20. 2013. pp. 890-896.

Chinese Search Report dated Apr. 1, 2020, in connection with corresponding CN Application No. 2017112909377 7 pp., including machine-generated English translation).

Extended European Search Report dated Sep. 14, 2021, in connection with corresponding EP Application No. 18885738.7; 7 pages.

\* cited by examiner

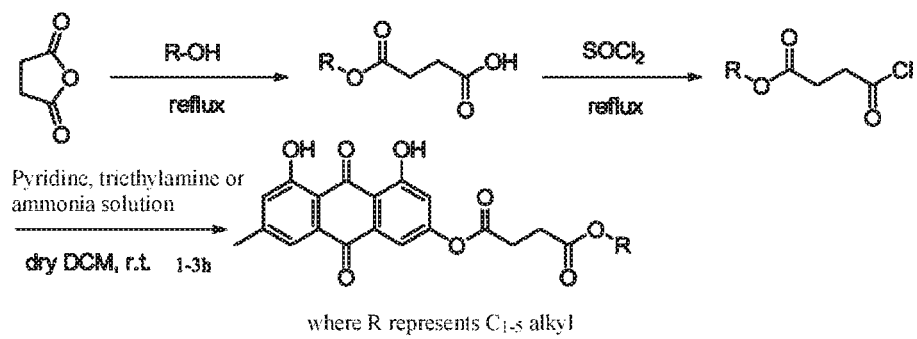
[FIG. 1]
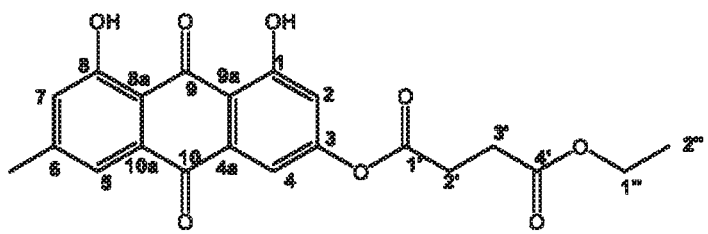
[FIG. 2]

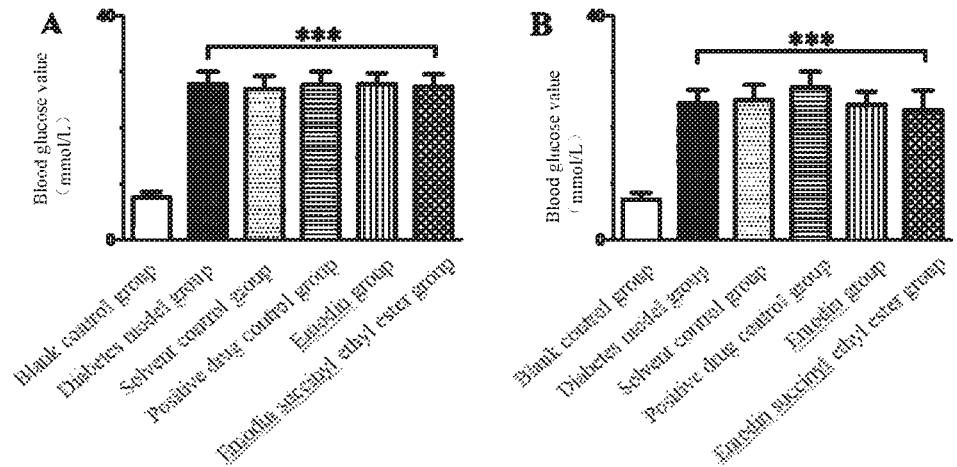
[FIG. 3]
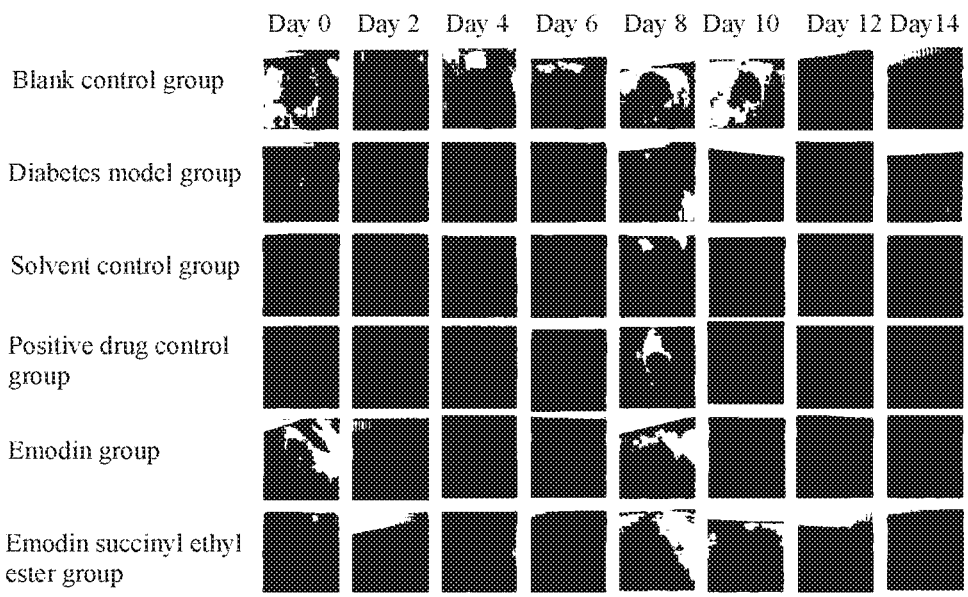
[FIG. 4]

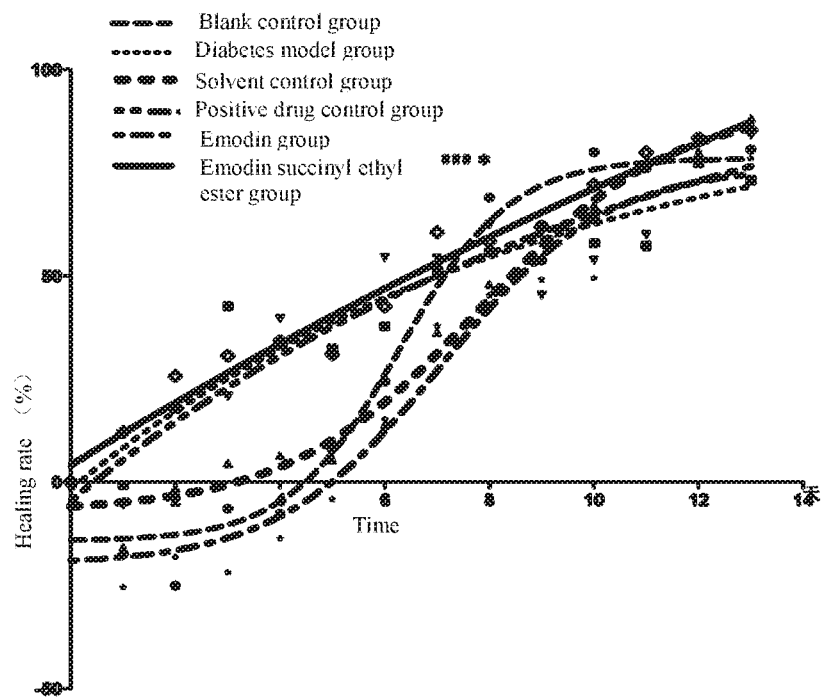
[FIG. 5]
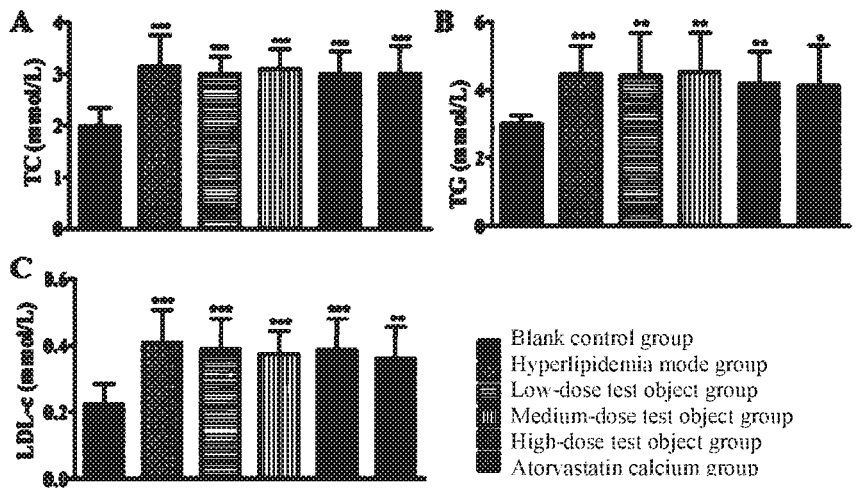
[FIG. 6]

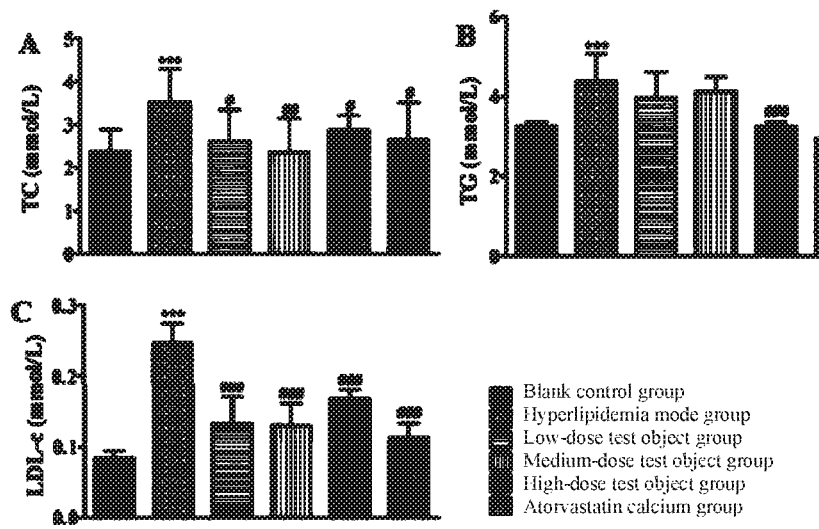
[FIG. 7]
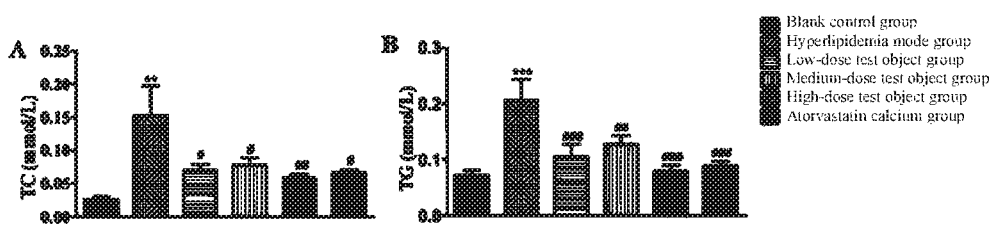
[FIG. 8]
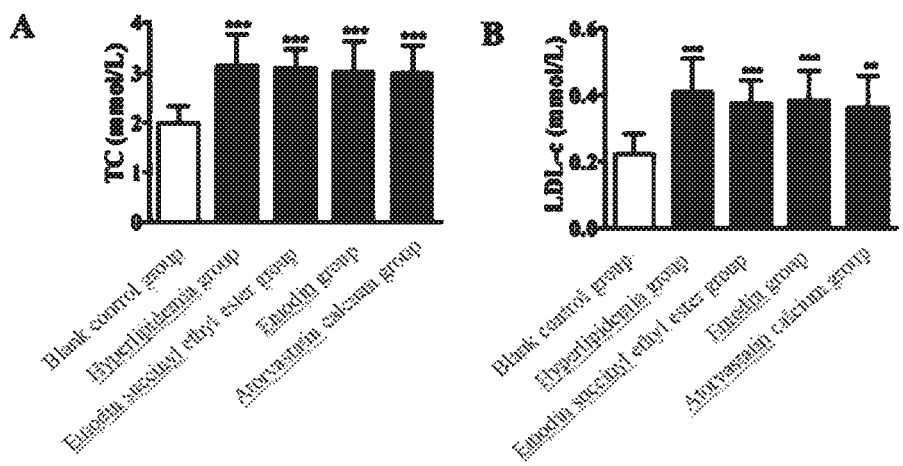
[FIG. 9]

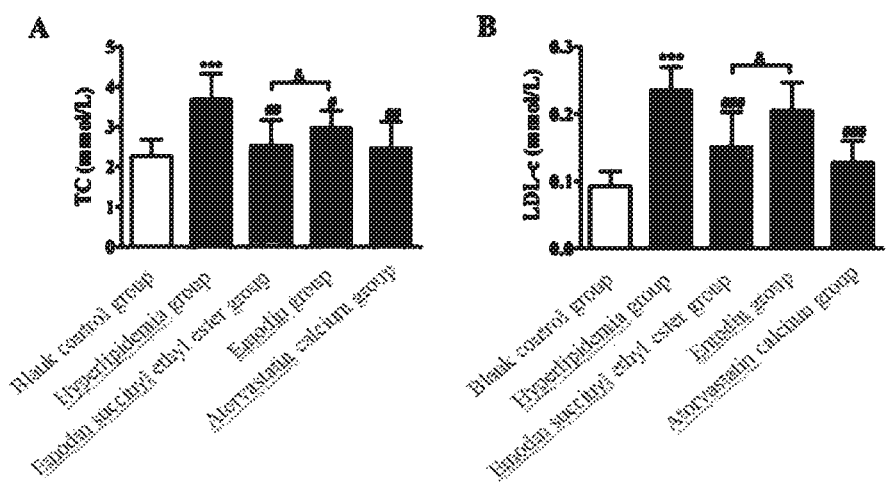
[FIG. 10]
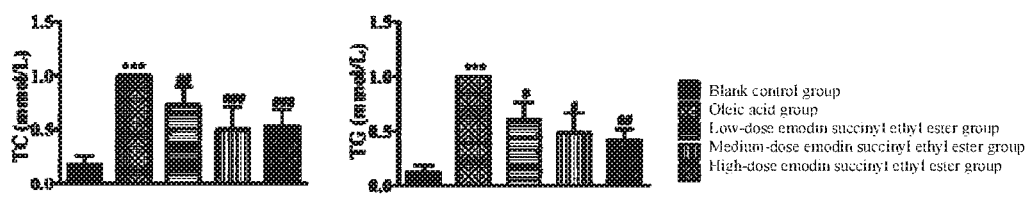
[FIG. 11]

EMODIN SUCCINYL ESTER COMPOUND, PREPARATION METHOD THEREFOR AND APPLICATION THEREOF

This application is a national stage entry under 35 U.S.C. 371 of PCT Application No. PCT/CN2018/118698, filed Nov. 30, 2018, which claims priority to China Patent Application No. 201711288330.5, filed Dec. 7, 2017, and China Patent Application No. 201711290937.7, filed Dec. 7, 2017, the entire contents of each of which are incorporated herein by reference

TECHNICAL FIELD

The present invention belongs to the fields of pharmaceutical synthesis and medicine and health. In particular, it relates to an emodin succinyl ester compound and a preparation method thereof and also relates to the application of the compound in promoting the healing of diabetic wounds and reducing blood lipid.

BACKGROUND

With the improvement of living standards, people's dietary structure has changed, the intake of cholesterol and saturated fatty acids has increased significantly, but the physical activities are relatively insufficient, resulting in the incidence of hyperlipidemia rising year by year. Hyperlipidemia, referring to high blood lipid levels, such as an increase in total cholesterol (TC) and triglyceride (TG) and low density lipoprotein (LDL-C) in the serum and a decrease in high density lipoprotein (HDL-C), can directly cause some diseases that seriously endanger human health, such as atherosclerosis and coronary heart disease. Hyperlipidemia can also cause diseases such as fatty liver, liver cirrhosis, cholelithiasis, pancreatitis, peripheral vascular disease and hyperuricemia. Clinical studies have shown that most patients with sudden cardiac death have coronary artery sclerosis lipid abnormalities and coronary artery sclerosis lipid abnormalities may play an important role in ischemic cardiovascular and cerebrovascular events. Disorders of lipid metabolism aggravate disorders of glucose metabolism on the one hand and increase the incidence and mortality of diabetic macrovascular complications, on the other hand.

Most of the commonly used lipid-regulating drugs in clinical practice are chemical synthetic preparations, which need to be taken for a long time. Various statins, such as simvastatin and lovastatin, can prevent cardiovascular and cerebrovascular accidents while treating hyperlipidemia. However, long-term or large-dose use of statins may lead to serious adverse reactions such as biochemical changes of liver tissue cells or cardiac rhabdomyolysis, thus limiting the long-term use of the statins. Therefore, it is of great significance to research and develop new and effective lipid-regulating drugs.

At present, diabetes has become the third chronic non-communicable disease that threatens human health worldwide. China is the country with the most diabetic patients in the world. In 2016, the estimated prevalence of diabetes diagnosed according to the latest international clinical diagnostic standards among adult samples aged 18 and over in China has reached 11.6%. About 30%-80% of the diabetic patients have skin lesions, which are manifested as tissue destruction in the feet or lower limbs, causing ulcers, infections and difficult-to-heal wounds, also known as diabetic foot. Diabetic foot is an important complication of diabetes and can lead to amputation in severe cases. The results of epidemiological investigations show that the probability of amputation of the lower limbs of patients with diabetes is 25 times higher than that of people without the disease and in some countries, diabetes causes an amputation even every 30 seconds. In addition, the cost of treatment and care for diabetic foot is also very high. The data shows that the cost of treatment and care for diabetic foot without primary ischemic symptoms in the first stage of healing is about $16,000. If a patient has the diabetic foot combined with major ischemic symptoms, the treatment cost of the patient will increase to $26,700; the cost of treatment and care for minor post-amputee healing is approximately $ 43,000, while the cost of treatment for major post-amputee healing increases to $ 63,100; in developing countries, at least 40% of the treatment cost for diabetes and its complications is for the treatment and care for diabetic foot. It can be seen that diabetic foot has caused a huge economic burden and social burden to the society, and the problem of diabetic wound healing disorders needs to be solved urgently.

Wound healing disorders seriously affect people's daily life, and effective prevention and treatment of diabetic wound healing disorders has important clinical significance. The current clinical treatment methods are generally supportive, such as: systemic therapies such as correction of dyslipidemia, correction of anemia and hypoalbuminemia, improvement of malnutrition, anti-infective therapy, improvement of microcirculation, improvement or nourishment of neurological function, hyperbaric oxygen therapy, surgical treatment and stem cell transplantation. These treatment methods are not only costly and unbearable for most patients, but also have unsatisfactory treatment effects. Therefore, research and development of effective drugs to promote the healing of diabetic wounds, speeding up the early healing process of diabetic wounds to shorten the process of diabetic wound healing and reduce the disability rate are the key issues in the medical field.

Emodin (1,3,8-trihydroxy-6-methylanthraquinone) is a major effective monomer that exists in the rhizomes and the senna leaves of Rheum, Polygonum and Rhamnus and is a plant-based drug. In recent years, many scholars have studied the pharmacological effects and mechanisms of emodin, and found that emodin has a wide range of pharmacological effects such as lowering blood lipids, antibacterial, anti-inflammatory and antitumor effects, inhibiting cell proliferation, improving immunity, and protecting liver and kidneys. Emodin has a significant lipid-lowering effect and has little toxic and side effects. However, due to the low bioavailability of emodin, the absolute bioavailability in male SD rats is 7.5% and is only 5% in females. The emodin succinyl ester compound disclosed in the present invention is obtained through structural modification of emodin, and the pharmacodynamic evaluation of emodin succinyl ethyl ester for lowering blood lipids was performed, and it was found that emodin succinyl ethyl ester had a significant effect on the treatment of hyperlipidemia and its blood lipid lowering effect was significantly better than that of emodin at the same dose. The present invention uses atorvastatin calcium as a main control drug, with an intention to observe the pharmacological effect of the emodin succinyl ester compound of the present invention on experimental rats with mixed hyperlipidemia. In addition, chemically modified emodin succinyl ester compounds can show better effects in promoting the healing of diabetic wounds than emodin. Therefore, it is necessary to modify emodin.

SUMMARY

In view of the shortcomings in the prior arts, the present invention provides a new compound for lowering blood lipids and promoting healing of diabetic wounds and application thereof. The compound provided by the present invention has the advantages of significant blood lipid lowering effect, good safety, simple and convenient medication, low price, convenient transportation and storage, and the like. In addition, the emodin succinyl ester compound can better promote the healing of diabetic wounds than emodin, and can be used to prepare drugs for promoting the healing of diabetic wounds. The synthesis route of the present invention is simple, can effectively save synthesis time and reduce cost, is simple to operate, is easy to implement, and is suitable for industrial production.

The present invention achieves the above objectives through the following technical solutions:

An emodin succinyl ester compound, having a structure represented by Formula I:

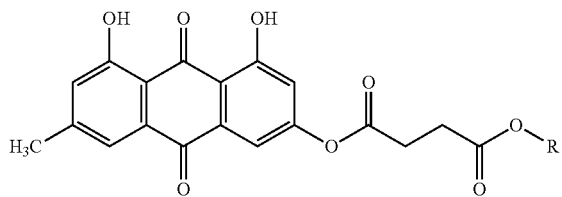

Formula I where R represents $C_{1-5}$ alkyl.

Preferably, in Formula I, R represents ethyl, that is, the emodin succinyl ester compound is emodin succinyl ethyl ester, having a chemical name of 1,8-dihydroxy-3-succinic acid monoethyl group-6-Methylanthraquinone, a molecular formula of $C_{21}H_{18}O_8$, and a molecular weight of 398.

Further, the present invention also provides a method for preparing the emodin succinyl ester compound, comprising the following steps: synthesizing monoalkanol succinate by using succinic anhydride and a $C_{1-5}$ alkanol; causing the monoalkanol succinate to react with sulfoxide chloride to obtain succinate monoalkanol ester acyl chloride; and causing the succinate monoalkanol ester acyl chloride to react with emodin to obtain the emodin succinyl ester compound.

Specifically, the method is implemented as in the following steps:

(1) Synthesis of monoalkanol succinate: placing succinic anhydride in a round-bottomed flask, carrying out heating reflux in the presence of $C_{1-5}$ alkanol as solvent, and carrying out reduced-pressure distillation to remove excess alkanol, thus obtaining a pale yellow oily substance, i.e., monoalkanol succinate, wherein the product is directly subjected to the next reaction without separation;

(2) Synthesis of succinate monoalkanol ester acyl chloride compound: placing the monoalkanol succinate in a round-bottomed flask, carrying out heating reflux in the presence of a solvent, sulfoxide chloride, and carrying out reduced-pressure distillation to remove excess sulfoxide chloride, thus obtaining a pale yellow to yellow oily substance, i.e., the succinate monoalkanol ester acyl chloride compound, wherein the product is directly subjected to the next reaction without separation;

(3) Synthesis of an emodin succinyl ester compound: placing emodin and alkali in a round-bottomed flask, slowly adding the corresponding succinate monoalkanol ester acyl chloride dropwise in the presence of dichloromethane as solvent, and reacting at room temperature;

(4) extracting with a sodium hydrogen carbonate solution, combining organic phases, extracting the organic phases with saturated brine, combining organic phases, drying with anhydrous sodium sulfate, filtering, and concentrating under reduced pressure to obtain a crude product which is a yellow to purple-yellow solid; and (5) chromatographing the crude product on a silica gel column and eluting with a dichloromethane-methanol mixed solution to obtain a pale yellow to yellow pure product, which is the corresponding emodin succinyl ester compound.

Further, when R represents ethyl, that is, when the emodin succinyl ester compound is emodin succinyl ethyl ester, the method is performed according to the following steps:

(1) Synthesis of monoethyl succinate: placing succinic anhydride in a round-bottomed flask, carrying out heating reflux in the presence of ethyl alcohol as solvent, and carrying out reduced-pressure distillation to remove excess ethyl alcohol, thus obtaining a pale yellow oily substance, i.e., monoethyl succinate, wherein the product is directly subjected to the next reaction without separation;

(2) Synthesis of succinate monoethyl ester acyl chloride: placing the monoethyl succinate in a round-bottomed flask, carrying out heating reflux in the presence of a solvent, sulfoxide chloride, and carrying out reduced-pressure distillation to remove excess sulfoxide chloride, thus obtaining a pale yellow oily substance, i.e., the succinate monoethyl ester acyl chloride, wherein the product is directly subjected to the next reaction without separation;

(3) Synthesis of emodin succinyl ethyl ester: placing emodin and alkali in a round-bottomed flask, slowly adding succinate monoethyl ester acyl chloride dropwise in the presence of dichloromethane as solvent, and reacting at room temperature;

(4) extracting with a sodium hydrogen carbonate solution, combining organic phases, extracting the organic phases with saturated brine, combining organic phases, drying with anhydrous sodium sulfate, filtering, and concentrating under reduced pressure to obtain a crude product which is a purple-yellow solid; and (5) chromatographing the crude product on a silica gel column and eluting with a dichloromethane-methanol mixed solution to obtain a pale yellow pure product, which is emodin succinyl ethyl ester.

Preferably, in the above method, the alkali in step (3) is selected from weak alkalis.

Further, in step (1), the time of heating reflux is 3-10 hours, preferably 4 hours, and the ratio (g:ml) of the mass of succinic anhydride to the volume of ethanol is 1:10, preferably 1:4; in step (2), the time of heating reflux is 1-10 hours, preferably 2 hours, and the mass ratio of monoethyl succinate to sulfoxide chloride is 1:1-1:10, preferably 1:4; in step (3), the alkali is pyridine, triethylamine, or ammonia, preferably pyridine, and the mass ratio of emodin to succinate monoethyl ester acyl chloride is 1:0.5-1, preferably 1:0.7; in step (5), in the dichloromethane-methanol mixed solution, the volume ratio of dichloromethane to methanol is 100:1-100:4, preferably 100:1.

The present invention further provides the application of the aforementioned emodin succinyl ester compound in the preparation of a drug for promoting the healing of diabetic wounds. The emodin succinyl ester compound is preferably emodin succinyl ethyl ester.

The present invention further provides a drug, comprising the aforementioned emodin succinyl ester compound. The emodin succinyl ester compound is preferably emodin succinyl ethyl ester.

Specifically, the drug may be a lipid-lowering drug or a drug for promoting healing of diabetic wounds.

Further, the drug is selected form cream, oil, patche, powders, spray, sustained release preparation, capsule, tablet, granule, injection or other preparations which is prepared by adding excipients required for the formulation of the preparations.

The present invention further provides an oily preparation, comprising the aforementioned emodin succinyl ester compound and a vegetable oil. The emodin succinyl ester compound is preferably emodin succinyl ethyl ester.

The present invention further provides a method for preparing the oily preparation, comprising the following steps:

(1) heating vegetable oil to a browned state for sterilization, resting at room temperature, and cooling for later use;

(2) weighing and dissolving the emodin succinyl ester compound according to claim 1 or 2 under an aseptic condition and in the vegetable oil after sterilization in step (1); wherein, preferably, the ratio (mg:ml) of the mass of the succinyl ester compound to the volume of the vegetable oil is 1-5:1, and more preferably 4:1;

(3) carrying out ultrasonic vibration so that the emodin succinyl ethyl ester is fully dissolved to form a uniform oily preparation; and (4) diluting the oily preparation obtained in step (3) with sterile water, sub-packaging under an aseptic condition, sealing, and storing at room temperature for later use; wherein, preferably, in the oily preparation diluted with sterile water, the concentration of the emodin succinyl ester compound is 50-150 μg/mL, and more preferably 100 μg/mL.

The present invention further provides the application of the aforementioned emodin succinyl ester compound in the preparation of a drug for lowering blood lipids and/or for treating fatty liver. The emodin succinyl ester compound is preferably emodin succinyl ethyl ester.

Specifically, the lipid-lowering drug has the effect of reducing total cholesterol (TC), low-density lipoprotein (LDL-C) in the serum, and TC and triglycerides (TG) in the liver.

The novel lipid-lowering compound, the emodin succinyl ester compound, is easily absorbed for the organisms, and is beneficial to improving the utilization of oral drugs by organisms. Through pharmacological experiments on experimental rats with mixed hyperlipidemia, it was confirmed that the lipid-lowering compound emodin succinyl ethyl ester of the present invention has a significant lipid-lowering effect, and its lipid-lowering effect is significantly better than that of emodin.

Compared with the prior arts, the present invention has the following beneficial effect:

1. The research results of the present invention can effectively provide a basis for the development of new drugs for promoting the healing of diabetic wounds and lowering blood lipids, has huge economic benefits in the future, and can produce a wide range of social benefits, thus have broad application prospects.

2. The preparation route of the present invention is feasible and reasonable and cost-effective, uses less toxic and harmful reagents, and does not cause environmental pollution. The total yield of the prepared emodin succinyl ethyl ester can be up to 90% and the purity can be up to 98% or more. Therefore, the preparation route is suitable for mass industrial production.

3. The experiment proves that the emodin succinyl ester compound of the present invention can significantly speed up the healing of the skin wound of mice with type 1 diabetes.

4. The present invention also provides an oily preparation for effectively promoting the healing of diabetic wounds and a preparation method thereof. The oily preparation takes an emodin succinyl ester compound as the unique effective ingredient and can effectively promote skin tissue repair and wound healing in patients with diabetes; in addition, the oily preparation can be used for large-scale production and preparation of drugs for treating the delayed wound healing of diabetic patients.

5. The oily preparation of the present invention, which can effectively promote the healing of diabetic wounds, can be mass-produced and used to treat the symptoms of wound healing disorders of diabetic patients and can take the effects of promoting skin tissue wound repair and the like.

6. The emodin succinyl ester compound can significantly regulate blood lipids. Compared with the most commonly used atorvastatin at the maximum clinical dose, it can significantly reduce the TC and LDL in serum and the TC and TG in liver. It can be used as a safe and effective drug for the prevention and treatment of hyperlipidemia. The emodin succinyl ester compound can significantly regulate blood lipids, and its effect of reducing the TC and LDL-C in serum is significantly better than that of emodin at the same dose.

7. High safety: The novel lipid-lowering compound of the present invention, i.e., the emodin succinyl ester compound, has a high tolerance dose and has no obvious toxic or side effects.

8. Medication is simple and convenient, and oral administration facilities the absorption by human or animals. The present invention can be transported and stored conveniently and it is sealed and stored in a cool and dry place.

9. The active pharmaceutical ingredient of the present invention is emodin, and the finished product has strong drug-forming properties. Compared with other imported lipid-lowering drugs, the present invention is low in price and highly cost-effective and thus is acceptable for patients.

BRIEF DESCRIPTION OF THE DRAWINGS

FIG. 1 is a synthetic route map of an emodin succinyl ester compound.

FIG. 2 is a schematic diagram of two-dimensional nuclear magnetic resonance related signals of emodin succinyl ethyl ester.

FIG. 3 shows the blood glucose values of mice in each group, where, A: blood glucose value of mice in each group after the establishment of a diabetes model; B: blood glucose value of mice in each group before the end of administration, the values are expressed as mean±standard error; after STZ administration, the successfully modeled animals were randomly divided into model control group, solvent control group, positive drug (recombinant human epidermal growth factor) control group, emodin group, and emodin succinyl ethyl ester according to blood glucose levels, 6 mice per group (': compared with the blank control group, P<0.001, n=6).

FIG. 4 is an illustrative diagram of the effect of emodin succinyl ethyl ester on wound healing in mice.

FIG. 5 is a fitting curve plot of the effect of emodin succinyl ethyl ester on the wound healing rate of mice, where, values are expressed as mean±standard error; *: compared with the model group, P<0.05; ####: compared with the emodin succinyl ethyl group, P<0.001, n=4-6).

FIG. 6 shows the levels of TC, TG and LDL-c in the serum of animals after the establishment of a hyperlipidemia model, where, data are expressed as mean±standard error, *P<0.05 vs. blank control group, **P<0.01 vs. blank control group, blank control group, n=10; hyperlipidemia model group, n=10; low-dose test object group, n=10; medium-dose test object group, n=10; high-dose test object group, n=10; atorvastatin calcium group: positive control drug group, n=11.

FIG. 7 shows the effect of emodin succinyl ethyl ester on the blood lipid levels in rats with mixed hyperlipidemia, where, data are expressed as mean±standard error, *P<0.05 vs. blank control group, P<0.01 vs. blank control group, *P<0.001 vs. blank control group, #P<0.05 vs. hyperlipidemia model group, ##P<0.01 vs. hyperlipidemia model group, ###P<0.001 vs. hyperlipidemia model group; blank control group, n=10; hyperlipidemia model group, n=10; low-dose test object group, n=10; medium-dose test object group, n=10; high-dose test object group, n=10; atorvastatin calcium group: positive control drug group, n=11.

FIG. 8 shows the effect of emodin succinyl ethyl ester on the levels of TC and TG in the liver of rats with mixed hyperlipidemia, where data are expressed as mean±standard error, *P<0.05 vs. blank control group, P<0.01 vs. blank control group, *P<0.001 vs. blank control group, #P<0.05 vs. hyperlipidemia model group, ##P<0.01 vs. hyperlipidemia model group, ###P<0.001 vs. hyperlipidemia model group; blank control group, hyperlipidemia model group, and low-dose test object group, medium-dose test object group, high-dose test object group and atorvastatin calcium group: positive control drug group, n=5 for each group.

FIG. 9 shows the levels of TC and LDL-c in animal serum after the establishment of a hyperlipidemia model, where, data are expressed as mean±standard error, *P<0.05 vs. blank control group, P<0.01 vs. blank control group, *P<0.01 vs. blank control group, blank control group, n=10; hyperlipidemia model group, n=10; test object (emodin succinyl ethyl ester) group, n=10; emodin group, n=10; atorvastatin calcium group: positive control group, n=11.

FIG. 10 shows comparison of the effects of emodin succinyl ethyl ester and emodin in lowering blood lipid levels in rats with mixed hyperlipidemia, where, data are expressed as mean±standard error, *P<0.05 vs. blank control group, P<0.01 vs. blank control group, *P<0.001 vs. blank control group, #P<0.05 vs. hyperlipidemia model group, ##P<0.01 vs. hyperlipidemia model group, ###P<0.001 vs. hyperlipidemia model group, &P<0.05 vs. emodin group; blank control group, n=10; hyperlipidemia model group, n=10; test object (emodin succinyl ethyl ester) group, n=10; emodin group, n=10; atorvastatin calcium group: positive control drug group, n=11.

FIG. 11 shows the effect of emodin succinyl ethyl ester on the levels of TC and TG in oleic acid-induced hyperlipemia cells.

where, data are expressed as mean±standard error, ***P<0.001 vs. blank control group, #P<0.05 vs. oleic acid group, ##P<0.01 vs. oleic acid group, ###P<0.001 vs. oleic acid group, blank control group, n=6; oleic acid group, n=6; low-dose test object (emodin succinyl ethyl ester in a dose of 5 μmol/L) group, n=6; medium-dose test object (emodin succinyl ethyl ester in a dose of 10 μmol/L) group, n=6; high-dose test object (emodin succinyl ethyl ester in a dose of 20 μmol/L) group, n=6.

DETAILED DESCRIPTION OF EMBODIMENTS

The present invention is further described below with reference to specific embodiments. The advantages and features of the present invention will become more clear with the description. However, these embodiments are only exemplary and do not limit the scope of the present invention in any way. Those skilled in the art should understand that the details and forms of the technical solutions of the present invention can be modified or replaced without departing from the spirit and scope of the present invention, but these modifications and replacements fall within the scope of the present invention.

Example 1 Preparation of Emodin Succinyl Ethyl Ester

Succinic anhydride (1.0 g, 10 mmol) is placed in a 10 ml round-bottomed flask and is subjected to heating reflux for 4 hours in the presence of ethyl alcohol (3.5 mL, 60 mmol) as solvent, and excess ethyl alcohol is removed by reduced-pressure distillation, and then a pale yellow oily substance, i.e., monoethyl succinate (1.4 g, 96%), is obtained. The product is directly subjected to the next reaction without separation.

The monoethyl succinate (1.0 g, 6.8 mmol) is placed in a 10 ml round-bottomed flask and is subjected to heating reflux for 2 hours in the presence of a solvent, sulfoxide chloride (4.0 g, 34.0 mmol), and excess sulfoxide chloride is removed by reduced-pressure distillation, and then a pale yellow oily substance, i.e., succinate monoethyl ester acyl chloride (1.1 g, 98%), is obtained. The product is directly subjected to the next reaction without separation.

Emodin (1.0 g, 3.7 mmol) and pyridine (0.45 g, 5.6 mmol) are placed in a 10 mL round-bottomed flask, and succinate monoethyl ester acyl chloride (0.7 g, 4.0 mmol) is added dropwise in a slow manner in the presence of a solvent dichloromethane (3 mL) at 0° C. and reacted at room temperature for 3 hours.

The reaction product is extracted with a sodium hydrogen carbonate solution (2 mL×3); organic phases are combined and extracted with saturated brine (3 mL×3); organic phases are combined, dried with anhydrous sodium sulfate, filtered, and concentrated under reduced pressure to obtain a crude product which is a purple-yellow solid.

The crude product is chromatographed on a silica gel column and eluted with a dichloromethane-methanol mixed solution (v/v 100:1) to obtain 1.4 g of a pale yellow pure product. The yield of the pure product is 94.7% and the purity of the pure product is 97%.

The synthetic route map of the emodin succinyl ester compound is shown in FIG. 1, where R represents ethyl.

Example 2 Preparation of Emodin Succinyl Ethyl Ester

Succinic anhydride (10 g, 100 mmol) is placed in a 150 ml round-bottomed flask and is subjected to heating reflux for 6 hours in the presence of ethyl alcohol (40 mL, 600 mmol) as solvent, and excess ethyl alcohol is removed by reduced-pressure distillation, and then a pale yellow oily substance, i.e., monoethyl succinate (14 g, 96%), is obtained. The product is directly subjected to the next reaction without separation.

The monoethyl succinate (10 g, 68 mmol) is placed in a 150 ml round-bottomed flask and is subjected to heating reflux for 2 hours in the presence of sulfoxide chloride (40 g, 340 mmol) as solvent, and excess sulfoxide chloride is removed by reduced-pressure distillation, and then a pale yellow oily substance, i.e., succinate monoethyl ester acyl chloride (11 g, 98%), is obtained. The product is directly subjected to the next reaction without separation.

Emodin (10 g, 37 mmol) and pyridine (2.3 g, 22 mmol) are placed in a 250 mL round-bottomed flask, and succinate monoethyl ester acyl chloride (7 g, 40 mmol) is added dropwise in a slow manner in the presence of dichloromethane (3 mL) as solvent at 0° C. and reacted at room temperature for 3 hours. The reaction product is extracted with a sodium hydrogen carbonate solution (20 mL×3); organic phases are combined and extracted with saturated brine (30 mL×3); organic phases are combined, dried with anhydrous sodium sulfate, filtered, and concentrated under reduced pressure to obtain a crude product which is a purple-yellow solid.

The crude product is chromatographed on a silica gel column and eluted with a dichloromethane-methanol mixed solution (v/v 100:1) to obtain 12.7 g of a pale yellow pure product. The yield of the pure product is 92.3% and the purity of the pure product is 98% or above.

The synthetic route map of the emodin succinyl ester compound is shown in FIG. 1, where R represents ethyl.

Example 3 Preparation of Emodin Succinyl Ethyl Ester

Succinic anhydride (10 g, 100 mmol) is placed in a 150 ml round-bottomed flask and is subjected to heating reflux for 2 hours in the presence of ethyl alcohol (20 mL, 434 mmol) as solvent, and excess ethyl alcohol is removed by reduced-pressure distillation, and then a pale yellow oily substance, i.e., monoethyl succinate (14 g, 96%), is obtained. The product is directly subjected to the next reaction without separation.

The monoethyl succinate (10 g, 68 mmol) is placed in a 150 ml round-bottomed flask and is subjected to heating reflux for 1 hours in the presence of sulfoxide chloride (20 g, 170 mmol) as solvent, and excess sulfoxide chloride is removed by reduced-pressure distillation, and then a pale yellow oily substance, i.e., succinate monoethyl ester acyl chloride (8 g, 98%), is obtained. The product is directly subjected to the next reaction without separation.

Emodin (10 g, 37 mmol) and pyridine (1.5 g, 44 mmol) are placed in a 250 mL round-bottomed flask, and succinate monoethyl ester acyl chloride (8 g, 45 mmol) is added dropwise in a slow manner in the presence of dichloromethane (3 mL) as solvent at room temperature and reacted at room temperature for 1 hour. The reaction product is extracted with a sodium hydrogen carbonate solution (20 mL×3); organic phases are combined and extracted with saturated brine (30 mL×3); organic phases are combined, dried with anhydrous sodium sulfate, filtered, and concentrated under reduced pressure to obtain a crude product which is a purple-yellow solid.

The crude product is chromatographed on a silica gel column and eluted with a dichloromethane-methanol mixed solution (v/v 100:1) to obtain 8 g of a pale yellow pure product. The yield of the pure product is 54.1% and the purity of the pure product is 98% or above.

The synthetic route map of the emodin succinyl ester compound is shown in FIG. 1, where R represents ethyl.

Example 4 Structure Identification of the Target Compound

The structure of the compounds prepared in Examples 1-3 was identified. The identification results showed that the compound was emodin succinyl ethyl ester, a yellow powder, dissolved in methanol, $[\alpha]_D^{26} 0.0°$ (c0.5, CHCl$_3$). IR (KBr, cm$_{-1}$) 3500 (—OH), 3088 (Ar—H), 2981 (RH), 1763 (C=O), 1730 (C=O), 1624 (benzene ring), 1481 (benzene ring). UV [nm (logε), MeOH]: 278 (3.37), 268 (3.40). CD (nm, Δε, MeOH): 212 (−0.56). In $_1$H-NMR, δ7.08 (1H, d, J=2.2 Hz) and 7.33 (1H, d, J=2.2 Hz) are proton signals coupled in meta position on the benzene ring. 67.39 (1H, brs) and 7.07 (1H, brs) are aromatic proton signals, δ2.91 (2H, d, J=6.2), 2.71 (2H, d, J=6.2 Hz), and 4.13 (2H, q, J=7.1 Hz) are three methylene proton signals, and δ 2.36 (3H, s) and 1.22 (3H, t, J=7.1 Hz) are methyl proton signals. The carbon spectrum gives 21 carbon signals, of which 6190.8 and 181.0 are ketocarbonyl carbon signals, δ172.0 and 170.6 are ester carbonyl carbon signals, and 163.2, 162.0 and 157.0 are oxygenated carbon signals on the benzene ring. In the $_1$H-$_1$HCOSY spectrum, δ2.91 and 2.71 have correlated signals, and 64.13 and 1.22 have correlated signals. According to the DEPT spectrum of the compound, the structure of the compound contains 4 sp2 hybridized methine carbon signals, 12 sp$_2$ hybridized quaternary carbon signals, 3 sp$_3$ hybridized methylene carbon signals, and 2 methyl carbon signals. Its hydrocarbon signals were assigned by HMQC spectrum. In the HMBC spectrum, the proton of δ7.08 is remotely correlated to chemical shifts of 163.2 and 114.3, the proton of δ7.33 is remotely correlated to carbon signals of 157.0, 181.0, and 114.3, the proton of δ7.39 is remotely correlated to carbon signals of δ149.5, 181.0, and 113.8, and the proton of δ7.07 is remotely correlated to the carbon signals of δ162.2 and 113.8. The proton at δ2.91 is remotely correlated with the carbon signal of δ170.6, the proton of δ2.71 is remotely correlated with the carbon signal of δ172.2, the proton of δ4.13 is remotely correlated with the carbon signal of δ172.2, the proton of δ1.22 is remotely correlated to the carbon signal of δ60.7, and the methyl proton of 2.36 is remotely correlated to the carbons of 121.1, 149.5, and 116.7. Based on the above information, the structure of the compound is determined as shown in Formula I below, and the signal assignment is shown in Table 1. Two-dimensional nuclear magnetic resonance (NMR) related signals of emodin succinyl ethyl ester are shown in Table 2.

Formula I

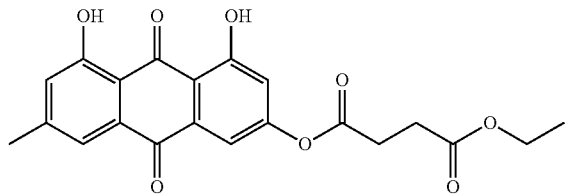

TABLE 1

NMR data (600 MHz, DMSO-d6) of emodin succinyl ethyl ester

| Position | $^1$H-NMR | $^{13}$C-NMR | DEPT | 1H-1H COSY | HMBC |
|---|---|---|---|---|---|
| 1 | — | 163.2 | C | — | — |
| 2 | 7.08 (1H, d, J = 2.2 Hz) | 124.6 | —CH— | H-4 | C-1,9a |
| 3 | — | 157.0 | C | — | — |
| 4 | 7.33 (1H, d, J = 2.2 Hz) | 113.4 | —CH— | H-2 | C-3,10,9a |
| 5 | 7.39(1H, brs) | 121.1 | —CH— | H-7 | C-6,10,8a |
| 6 | — | 149.5 | C | — | — |
| 7 | 7.07(1H, brs) | 116.7 | —CH— | H-5 | C-8,8a |
| 8 | — | 162.0 | C | — | — |
| 9 | — | 190.8 | C | — | — |
| 10 | — | 181.0 | C | — | — |
| 4a | — | 135.0 | C | — | — |
| 8a | — | 113.8 | C | — | — |
| 9a | — | 114.3 | C | — | — |
| 10a | — | 135.0 | C | — | — |
| 1' | — | 170.6 | C | — | — |
| 2' | 2.91(2H, d, J = 6.2) | 29.5 | —CH$_2$— | H-2' | C-1' |
| 3' | 2.71 (2H, d, J = 6.2 Hz) | 29.0 | —CH$_2$— | H-3' | C-4' |
| 4' | — | 172.2 | C | — | — |
| 1" | 4.13 (2H, q, J = 7.1 Hz) | 60.7 | —CH$_2$— | H-1" | C-4' |
| 2" | 1.22 (3H, t, J = 7.1 Hz) | 14.5 | —CH$_3$ | H-2" | C-1" |
| 6—CH$_3$ | 2.36(3H, s) | 22.0 | —CH$_3$ | — | C-5,6,7 |

Example 5 Efficacy Test 1 of the Product of the Present Invention

1. Preparation of Drug (1) Preparation of Emodin Succinyl Ethyl Ester Oil

① weighing 10 mg of emodin succinyl ethyl ester (prepared in Examples 1-3) in 2.5 mL of vegetable oil cooled after boiling;

② carrying out ultrasonic vibration for 10 minutes so that the emodin succinyl ethyl ester is fully dissolved; and ③ diluting the emodin succinyl ethyl ester to 100 μg/mL with the aseptically cooled vegetable oil, aseptically sub-packaging, sealing and storing at room temperature for later use.

(2) Preparation of Emodin Oil

① weighing 10 mg of emodin in 2.5 mL of vegetable oil cooled after boiling;

② carrying out ultrasonic vibration for 10 minutes so that the emodin is fully dissolved; and ③ diluting the emodin to 200 μg/mL with the aseptically cooled vegetable oil, aseptically sub-packaging, sealing, and storing at room temperature for later use.

2. Experimental Methods 2.1 Establishment of a Mouse Diabetes Model

SPF-grade male Kunming mice (18-20 g) were adaptively fed with ordinary maintenance feed for 3-5 days, weighed and randomly divided into a blank control group (Control) and a diabetes model group. Mice in the diabetes model group were administrated with high-dose STZ (streptozotocin, 180 mg/kg) through intraperitoneal injection and fasting blood glucose was measured after one week. The mice successfully modeled were randomly divided into 5 groups, namely, the diabetes model group (Model), the solvent control group (Solvent), the positive drug (recombinant human epidermal growth factor) control group (EGF), the emodin group (DHS), and the emodin succinyl ethyl ester group (DHS-YSW).

2.2 Establishment of Mouse Wound Model

Animals in each group were anesthetized with sodium pentobarbital (1%) and shaved on the back. A 5 mm skin punch was used to establish a 5 mm wound model at the highest part of the back. The Control group and the Model group were not treated with any drugs. The solvent control group was dripped with 10 μL of sterile vegetable oil. The positive drug group was dripped with 10 μL of recombinant human epidermal factor solution (2000 IU/mL) each day. The other groups were dripped on the wound with 10 μL of a corresponding drug, once a day for 14 consecutive days.

2.3 Detection of Mouse Wound Area

During the experiment, fixed-height fixed-focus photographs were taken daily to record the wound healing status of each group of mice. Image-Pro-Plus software was used to determine the wound area, and statistical analysis was performed on the wound healing status of each group of mice to estimate the effect of emodin succinyl ethyl ester oil on the wound healing process of mice with diabetes.

Wound healing rate=(wound area on day 0−wound area on day N)/wound area on day 0*100%

2.4 Statistical Methods

The experimental data were expressed as mean±standard error. One-way ANOVA and T-test were used to statistically analyze the blood glucose values of the mice in each group. One-way ANOVA and paired T-test were used to statistically analyze the differences in wound healing rates of the mice. P<0.05 indicates significant differences. The experimental results were all analyzed and graphed using Graphpad-Prism6.0.

3. Experimental Results 3.1 Blood Glucose of Each Group of Animals

The results are shown in FIG. 3. It can be seen from FIG. 3 that after the high-dose STZ administration, the blood glucose levels of mice in the diabetes model group, the solvent control group, the positive drug control group (recombinant human epidermal growth factor, EGF), the emodin group, and the emodin succinyl ethyl ester group were significantly increased as compared with the blood glucose level of the blank control group (***P<0.001 vs. the blank control group). From the results, it can be seen that during the mouse wound healing experiment, except for the blank control group, the mice in each group were in a hyperglycemic state.

3.2 Effects of Emodin Succinyl Ethyl Ester on Wound Healing of Mice with Diabetes Results were shown in FIGS. 4 and 5, the mice in the diabetes model group had slower wound healing speed than the mice in the blank control group, while the mice in the emodin succinyl ethyl ester group had significantly faster wound healing speed than the mice in the diabetes model group, the solvent control group and the emodin group, and there were statistical differences (*P<0.05 vs. compared with the model group; ####P<0.001 vs. emodin group; ####P<0.001 vs. solvent control group). The results show that emodin succinyl ethyl ester can effectively speed up the wound healing of mice with diabetes, and has better curative effect than solvent and emodin, and its efficacy is stable and significant.

Example 6 Efficacy Test 1 of the Product of the Present Invention

1. Experimental Materials

Experimental animals: 61 rats of uniform weight

Test object: Emodin succinyl ethyl ester (prepared in Examples 1-3)

High-fat feed: 20.0% of sucrose, 15.0% of lard, 1.2% of cholesterol, 0.2% of sodium cholate, an appropriate amount of casein, calcium hydrogen phosphate, stone powder, etc. were added to the maintenance feed. In addition to crude fat, the moisture, crude protein, crude fat, crude fiber, crude ash, calcium, and phosphorus of the model feed must meet the national standards for maintenance feed. The feed is clean grade, vacuum packed and stored at room temperature.

2. Experimental Principle

Feeding rats with high-fat feed containing cholesterol, sucrose, lard, and sodium cholate can form a rat model of lipid metabolism disorders, and then the rats are administrated with drug, detect the effect of the test object on hyperlipidemia, and determine the effect of the test object on the lipid absorption, lipoprotein formation, lipid degradation or excretion in rats.

Determination of mixed hyperlipidemia rat model: After the end of the modeling period, compared with the blank control group, rats in the hyperlipidemia model group have increased TG, TC or LDL-C in the serum, and the differences were significant, thus the establishment of the model is determined.

3. Experimental Methods

3.1 Animal Grouping

First random grouping: After the animals are received, they are adaptively fed for 5 to 7 days. During the domestication period, the appearance and general state of the rats are observed. Only qualified rats can enter this experiment. After the end of the adaptation period, the rats were weighed and randomly divided into a blank control group (10 rats) and a hyperlipidemia model group (51 rats).

Second random grouping: After the establishment of the rat hyperlipidemia model, the blood lipids of the rats were measured, and rats in the hyperlipidemia model group were randomly divided into five groups, 11 rats in the positive drug group, 10 rats in each of the other groups. The five groups were the hyperlipidemia model group, the low-dose test object group (emodin succinyl ethyl ester in a dose of 10 mg/kg·d$^{-1}$), the medium-dose test object group (emodin succinyl ethyl ester in a dose of 20 mg/kg·d$^{-1}$), the high-dose test object group (emodin succinyl ethyl ester in a dose of 40 mg/kg·d$^{-1}$), and the positive control drug group (Atorvastatin calcium group in a dose of 10 mg/kg·d$^{-1}$), respectively.

3.2 Establishment Period of Mixed Hyperlipidemia Model

The administration and diet of the animals in each group are shown in Table 2. In the experimental groups, rats in the blank control group were fed with maintenance feed and the remaining 5 groups were fed with high-fat diet. After 2 weeks, the levels of TG, TC, LDL-C and HDL-C in the serum of the rats were measured. The rats were weighed once a week.

Two weeks after the rats in the hyperlipidemia model group were given a high-fat diet, rats in the blank control group and the hyperlipidemia model group were not fasted to take blood from the tip of the tail. The serum was than separated and the levels of TC, TG, LDL-C and HDL-C in the serum were measured. According to the levels of TC, TG and LDL-C, the rats in the hyperlipidemia model group were randomly divided into 5 groups. After grouping, the hyperlipidemia model group, the low-dose test object group, the medium-dose test object group, the high-dose test object group, the positive control drug group (Atorvastatin calcium group) were compared with the blank control group in terms of TC, TG, LDL-C and HDL-C.

The changes in blood lipids of rats in the hyperlipidemia model group and each administration group compared with the blank control group were observed. The results are shown in Table 3 and FIG. 6. After the establishment of the mixed hyperlipidemia model, compared with rats in each administration group and rats in the blank group, the rats in the hyperlipidemia model group had significant increase in TC (\*\*\*P<0.001 vs. blank control group), TG (\*\*\*P<0.001 vs. blank control group), \*\*P<0.01 vs. blank control group, \*P<0.05 vs. blank control group) and LDL-C (\*\*\*P<0.001 vs. blank control group, \*\*P<0.01 vs. blank control group) in the serum, all with statistical differences, and there was no significant difference in TC, TG and LDL-C among the administration groups. In this case, it could be determined that the mixed hyperlipidemia model was successfully established.

TABLE 2

Drug administration and diet of animals in each group

| Group | Administration frequency | Administration cycle | Dose | Diet | Number of rats |
|---|---|---|---|---|---|
| Blank control group | Intragastrically administered once a day | Two weeks | 10 ml/kg (rat weight) | Normal | 10 |
| Hyperlipidemia model group | Intragastrically administered once a day | Two weeks | 10 ml/kg (rat weight) | High-fat | 10 |
| Low-dose test object group | Intragastrically administered once a day | Two weeks | 10 mg/kg (rat weight) | High-fat | 10 |
| Medium-dose test object group | Intragastrically administered once a day | Two weeks | 20 mg/kg (rat weight) | High-fat | 10 |
| High-dose test object group | Intragastrically administered once a day | Two weeks | 40 mg/kg (rat weight) | High-fat | 10 |
| Positive control drug group | Intragastrically administered once a day | Two weeks | 10 mg/kg (rat weight) | High-fat | 11 |

Table Levels of TC, TG, LDL-C and HDL-C in animal serum after the establishment of a hyperlipidemia model

| Group | TC (mmol/L) | TG (mmol/L) | LDL-C (mmol/L) |
|---|---|---|---|
| Blank control group | 1.99 ± 0.35 | 3.02 ± 0.25 | 0.22 ± 0.41 |
| Hyperlipidemia mode group | 3.15 ± 0.61\*\*\* | 4.51 ± 0.86\*\*\* | 0.41 ± 0.11\*\*\* |
| Low-dose test object group | 3.00 ± 0.33\*\*\* | 4.47 ± 1.33\*\* | 0.38 ± 0.09\*\*\* |
| Medium-dose test object group | 3.10 ± 0.3\*7\*\*\* | 4.49 ± 1.22\*\* | 0.37 ± 0.07\*\*\* |
| High-dose test object group | 3.00 ± 0.43\*\*\* | 4.15 ± 0.97\*\* | 0.39 ± 0.10\*\*\* |
| atorvastatin calcium group | 3.00 ± 0.53\*\*\* | 4.02 ± 1.16\* | 0.36 ± 0.10\*\* |

Note:
Data are expressed as mean ± standard error,
\*P < 0.05 vs. blank control group,
\*\*P < 0.01 vs. blank control group, blank control group, n = 10; hyperlipidemia model group, n = 10; low-dose test object group, n = 10; medium-dose test object group, n = 10; high-dose test object group, n = 10; atorvastatin calcium group: positive control drug group, n = 11.

3.3 Administration Period

The rats in the successfully grouped high-dose test object, medium-dose, and low-dose groups and positive control drug group (atorvastatin calcium group) were intragastrically administered daily. Rats in the blank control group and the hyperlipidemia model group were given corresponding doses of lysozyme. The doses of the groups are shown in Table 2.

Feeding conditions remained unchanged. The rats were weighed once a week. Blood were collected at the tip of the tail two weeks after drug administration and livers were taken, to determine the levels of TC, TG, LDL-C, and HDL-C in serum of the rats and the levels of TC and TG in the liver, and then the effect of the test object on the TC, TG, LDL-C and HDL-C in serum of the rats and the TC and TG in liver were observed.

3.4 Observation Period

General vital signs were observed during the experiment.

3.5 Main Detection Indicators (1) Weight, measured once a week.

(2) TC, TG, LDL-C and HDL-C in serum, measured once after the establishment of the hyperlipidemia model and two weeks after administration.

(3) TC and TG in liver, measured after sampling

4. Experimental Data and Results 4.1 Data Processing

The analysis of variance is performed, but the homogeneity of variance test needs to be performed first according to the procedure of analysis of variance. If the variance is homogeneous, the F value is calculated, and 36F<0.05. Conclusion: There is no significant difference between the means of all the groups; F≥0.05, P≤0.05 and the statistics are made using a pairwise comparison of means between multiple experimental groups and one control group; appropriate variable conversion is performed on non-normal or heterogeneous-variance data, the data are used for statistics after the data after conversion become normal and homogeneous-variance data; if the data after conversion still are non-normal and heterogeneous-variance data, rank sum test could be performed for statistics.

4.2 Determination of Animal Experiment Results

Determination of lipid-lowering effect: Compared with the blank control group, rats in the hyperlipidemia model control group had increased TG, TC or LDL-C in the serum, and the differences were significant, thus the establishment of the model is determined.

(1) Compared with the model control group, rats in any dose group had reduced TC or LDL-C in serum and the rats in any dose group had reduced TG, with significant differences; moreover, the level of HDL-C in serum of rats in each dose group was not significantly lower than that in the model control group; thus, it could be determined that the test sample had a positive result in the animal experiment on blood lipid lowering function.

(2) Compared with the model control group, rats in any dose group had reduced TC or LDL-C in serum, with significant differences; moreover, the TG in serum of rats in each dose group was not significantly higher than that in the model control group, and the level of HDL-C in serum of rats in each dose group was not significantly lower than that in the model control group; thus, it could be determined that the test sample had a positive result in the animal experiment on cholesterol lowering function.

(3) Compared with the model control group, rats in any dose group had reduced TG in serum, with significant differences; moreover, the TC and LDL-C in serum of rats in each dose group were not significantly higher than those in the model control group, and the level of HDL-C in serum of rats in each dose group was not significantly lower than that in the model control group; thus, it could be determined that the test sample had a positive result in the animal experiment on TG lowering function.

4.3 Experimental Results

The results are shown in Table 4 and FIG. 7. Two weeks after administration, compared with rats in the blank control group, rats in the mixed hyperlipidemia model group have significantly increased TC (* $P<0.001$ vs. blank control group), TG (* $P<0.001$ vs. blank control group) and LDL-C (*** $P<0.001$ vs. blank control group) in serum, thus determining the successful establishment of the model. Emodin succinyl ethyl ester in low, medium, high doses and atorvastatin calcium can significantly reduce TC (#$P<0.05$ vs. hyperlipidemia group) and LDL-C (#$P<0.05$ vs. hyperlipidemia group); emodin succinyl ethyl ester in a high dose and atorvastatin calcium can significantly reduce TG in serum of rats with hyperlipidemia (####$P<0.001$ vs. hyperlipidemia group).

TABLE 4

Effect of emodin succinyl ethyl ester on the blood lipid levels in rats with mixed hyperlipidemia

| Group | TC (mmol/L) | TG (mmol/L) | LDL-C (mmol/L) |
|---|---|---|---|
| Blank control group | 2.38 ± 0.52 | 3.24 ± 0.11 | 0.09 ± 0.02 |
| Hyperlipidemia mode group | 3.53 ± 0.76*** | 4.37 ± 0.69*** | 0.24 ± 0.04*** |
| Low-dose test object group | 2.60 ± 0.74# | 3.98 ± 0.63 | 0.17 ± 0.08# |
| Medium-dose test object group | 2.36 ± 0.78## | 4.12 ± 0.37 | 0.15 ± 0.05### |
| High-dose test object group | 2.88 ± 0.34# | 3.23 ± 0.12### | 0.18 ± 0.03## |
| Atorvastatin calcium group | 2.82 ± 1.02# | 2.94 ± 0.20### | 0.13 ± 0.03### |

Note:

Data are expressed as mean ± standard error,

*$P < 0.05$ vs. blank control group,

**$P < 0.01$ vs. blank control group,

***$P < 0.001$ vs. blank control group,

$P < 0.05$ vs. hyperlipidemia model group,

$P < 0.01$ vs. hyperlipidemia model group,

$P < 0.001$ vs. hyperlipidemia model group; blank control group, n = 10; hyperlipidemia model group, n = 10; low-dose test object group, n = 10; medium-dose test object group, n = 10; high-dose test object group, n = 10; atorvastatin calcium group: positive control drug group, n = 11.

The results are shown in Table 5 and FIG. 8. Two weeks after administration, compared with rats in the blank control group, rats in the mixed hyperlipidemia model group have significantly increased TC (* $P<0.001$ vs. blank control group) and TG (* $P<0.001$ vs. blank control group) in liver, thus determining the successful establishment of the model. Emodin succinyl ethyl ester in low, medium, high doses and atorvastatin calcium can reduce TC (#$P<0.05$ vs. hyperlipidemia model group) and TG (##$P<0.01$ vs. hyperlipidemia model group); emodin succinyl ethyl ester shows good effects of lowering blood lipid and protecting the liver, so it can be used for prevention or treatment of fatty liver.

TABLE 5

Effect of emodin succinyl ethyl ester on the levels of TC
and TG in the liver of rats with mixed hyperlipidemia

| Group | TC (mmol/L) | TG (mmol/L) |
|---|---|---|
| Blank control group | 0.027 ± 0.004 | 0.073 ± 0.008 |
| Hyperlipidemia mode group | 0.137 ± 0.052** | 0.206 ± 0.038*** |
| Low-dose test object group | 0.069 ± 0.010# | 0.105 ± 0.023### |
| Medium-dose test object group | 0.078 ± 0.010# | 0.127 ± 0.016## |
| High-dose test object group | 0.059 ± 0.005## | 0.079 ± 0.011### |
| Atorvastatin calcium group | 0.066 ± 0.004# | 0.090 ± 0.008## |

Note:
Data are expressed as mean ± standard error,
*$P < 0.05$ vs. blank control group,
**$P < 0.01$ vs. blank control group,
***$P < 0.001$ vs. blank control group,
$P < 0.05$ vs. hyperlipidemia model group,
$P < 0.01$ vs. hyperlipidemia model group,
$P < 0.001$ vs. hyperlipidemia model group; blank control group; hyperlipidemia model group; low-dose test object group; medium-dose test object group; high-dose test object group; and atorvastatin calcium group: positive control drug group, n = 5.

Example 7 Efficacy Test 3 of the Product of the Present Invention

1. Experimental Materials

Experimental animals: 51 rats of uniform weight

Test object: Emodin succinyl ethyl ester (prepared in Examples 1-3)

High-fat feed: 20.0% of sucrose, 15% of lard, 1.2% of cholesterol, 0.2% of sodium cholate, an appropriate amount of casein, calcium hydrogen phosphate, stone powder, etc. were added to the maintenance feed. In addition to crude fat, the moisture, crude protein, crude fat, crude fiber, crude ash, calcium, and phosphorus of the model feed must meet the national standards for maintenance feed. The feed is clean grade, vacuum packed and stored at room temperature.

2. Experimental Principle

Feeding rats with high-fat feed containing cholesterol, sucrose, lard and sodium cholate can form a rat model of lipid metabolism disorders and then the rats are administered with a drug, detect the effects of the test object on hyperlipidemia, and determine the effect of the test object on the lipid absorption, lipoprotein formation, lipid degradation or excretion in rats.

Determination of mixed hyperlipidemia rat model: After the end of the modeling period, compared with the blank control group, rats in the hyperlipidemia model group had increased TG, TC or LDL-C in the serum, and the differences were significant, thus the establishment of the model determined.

3. Experimental Methods 3.1 Animal Grouping

First random grouping: After the animals are received, they are adaptively fed for 5 to 7 days. During the domestication period, the appearance and general state of the rats are observed. Only qualified rats can enter this experiment. After the end of the adaptation period, the rats were weighed and randomly divided into a blank control group (10 rats) and a hyperlipidemia model group (41 rats).

Second random grouping: After the establishment of the rat hyperlipidemia model, the blood lipids of the rats were measured, and rats in the hyperlipidemia model group were randomly divided into four groups, 11 rats in the positive drug group, 10 rats in each of the other groups. The four groups were the hyperlipidemia model group, the low-dose test object (emodin succinyl ethyl ester in a dose of 20 mg/kg·d$^{-1}$) group, the emodin (20 mg/kg·d$^{-1}$) group, and the positive control drug (Atorvastatin calcium group in a dose of 10 mg/kg·d$^{-1}$) group, respectively.

3.2 Establishment Period of Mixed Hyperlipidemia Model

The administration and diet of the animals in each group are shown in Table 6. In the experimental groups, rats in the blank control group were fed with maintenance feed and the remaining 4 groups were fed with a high-fat diet. After 2 weeks, the levels of TG, TC, LDL-C and HDL-C in the serum of the rats were measured. The rats were weighed once a week.

Two weeks after the rats in the hyperlipidemia model group were given a high-fat diet, rats in the blank control group and the hyperlipidemia model group were not fasted to take blood from the tip of the tail. The serum was then separated and the levels of TC, TG, LDL-C and HDL-C in the serum were measured. According to the levels of TC, TG and LDL-C, the rats in the hyperlipidemia model group were randomly divided into 4 groups. After grouping, the hyperlipidemia model group, the test object (emodin succinyl ethyl ester in a dose of 20 mg/kg·d$^{-1}$) group, the emodin (20 mg/kg·d$^{-1}$) group, and the positive control drug (Atorvastatin calcium group in a dose of 10 mg/kg·d$^{-1}$) group were compared with the blank control group in terms of TC, TG, LDL-C and HDL-C.

The changes in blood lipids of rats in the hyperlipidemia model group and each administration group, compared with the blank control group, were observed. The results are shown in Table 7 and FIG. 9. After the establishment of the mixed hyperlipidemia model, compared with rats in each administration group and rats in the blank group, the rats in the hyperlipidemia model group had significant increase in TC (* $P<0.001$ vs. blank control group) and LDL-C ( $P<0.01$ vs. blank control group, *** $P<0.001$ vs. blank control group) in the serum, all with statistical differences, and there was no significant difference in TC and LDL-C among the administration groups. In this case, it could be determined that the mixed hyperlipidemia model was successfully established.

TABLE 6

Drug administration and diet of animals in each group

| Group | Administration frequency | Administration cycle | Dose | Diet | Number of rats |
|---|---|---|---|---|---|
| Blank control group | Intragastrically administered once a day | Two weeks | 10 ml/kg (rat weight) | Normal | 10 |
| Hyperlipidemia model group | Intragastrically administered once a day | Two weeks | 10 ml/kg (rat weight) | High-fat | 10 |
| Test object (emodin succinyl ethyl ester) group | Intragastrically administered once a day | Two weeks | 20 mg/kg (rat weight) | High-fat | 10 |
| Emodin group | Intragastrically administered once a day | Two weeks | 20 mg/kg (rat weight) | High-fat | 10 |
| Positive control drug group | Intragastrically administered once a day | Two weeks | 10 mg/kg (rat weight) | High-fat | 11 |

TABLE 7

Blood lipid level of rats after modeling

| Group | TC (mmol/L) | LDL-C (mmol/L) |
|---|---|---|
| Blank control group | 1.99 ± 0.35 | 0.22 ± 0.06 |
| Hyperlipidemia mode group | 3.15 ± 0.61*** | 0.41 ± 0.11*** |
| Emodin derivative group | 3.10 ± 0.37*** | 0.37 ± 0.07*** |
| Emodin group | 3.02 ± 0.06*** | 0.38 ± 0.09*** |
| Atorvastatin calcium group | 3.00 ± 0.53*** | 0.36 ± 0.10** |

Note:
Data are expressed as mean ± standard error,
*$P < 0.05$ vs. blank control group,
**$P < 0.01$ vs. blank control group,
***$P < 0.001$ vs. blank control group, blank control group, n = 10; hyperlipidemia model group, n = 10; test object (emodin succinyl ethyl ester) group, n = 10; emodin group, n = 10; atorvastatin calcium group, n = 11.

3.3 Administration Period

The rats in the successfully grouped test object (emodin succinyl ethyl ester) group, emodin group and positive control drug group (atorvastatin calcium group) were intragastrically administered daily. Rats in the blank control group and the hyperlipidemia model group were given corresponding doses of lysozyme. The doses of the groups are shown in Table 6.

Feeding conditions remained unchanged. The rats were weighed once a week. Blood were collected at the tip of the tail two weeks after drug administration. The effect of the test object on the TC, TG, LDL-C and HDL-C in serum of the rats were observed.

3.4 Observation Period

General vital signs were observed during the experiment.

3.5 Main Detection Indicators (1) Weight, measured once a week.

(2) TC, TG, LDL-C and HDL-C in serum, measured once after the establishment of the hyperlipidemia model and two weeks after administration.

4. Experimental Data and Results 4.1 Data Processing

The analysis of variance is performed, but the homogeneity of variance test needs to be performed first according to the procedure of analysis of variance. If the variance is homogeneous, the F value is calculated, and 36F<0.05. Conclusion: There is no significant difference between the means of all the groups; F≥0.05, P≤0.05, and the statistics are made using a pairwise comparison of means between multiple experimental groups and one control group; appropriate variable conversion is performed on non-normal or heterogeneous-variance data; after the data after conversion become normal and homogeneous-variance data, the data are used for statistics; if the data after conversion still are non-normal and heterogeneous-variance data, rank sum test could be performed for statistics.

4.2 Determination of Animal Experiment Results

Determination of lipid-lowering effect: Compared with the blank control group, rats in the hyperlipidemia model control group had increased TG, TC or LDL-C in the serum, and the differences were significant, thus the establishment of the model is determined.

(1) Compared with the model control group, rats in the test object group had reduced TC or LDL-C in serum and the rats in the test object group had reduced TG, with significant differences; moreover, the level of HDL-C in serum of rats in the test object group was not significantly lower than that in the model control group; thus, it could be determined that the test sample had a positive result in the animal experiment on blood lipid lowering function.

(2) Compared with the model control group, rats in the test object group had reduced TC or LDL-C in serum, with significant differences; moreover, the TG in serum of rats in the test object group was not significantly higher than that in the model control group, and the level of HDL-C in serum of rats in the test object group was not significantly lower than that in the model control group; thus, it could be determined that the test sample had a positive result in the animal experiment on cholesterol lowering function.

(3) Compared with the model control group, rats in the test object group had reduced TG in serum, with significant differences; moreover, the TC and LDL-C in serum of rats in the test object group were not significantly higher than those in the model control group, and the level of HDL-C in serum of rats in each dose group was not significantly lower than that in the model control group; thus, it could be determined that the test sample had a positive result in the animal experiment on TG lowering function.

4.3 Experimental Results

The results are shown in FIG. 10. Two weeks after administration, compared with rats in the blank control group, rats in the mixed hyperlipidemia model group have significantly increased TC (* $P<0.001$ vs. blank control group) and LDL-C (* $P<0.001$ vs. blank control group) in serum, thus determining the successful establishment of the model. The test object (emodin succinyl ethyl ester in a dose of 20 mg/kg·d$^{-1}$) can significantly reduce TC (#$P<0.05$ vs. hyperlipidemia group) and LDL-C (#$P<0.05$ vs. hyperlipidemia group) in serum of rats with hyperlipidemia, and it is obvious that the test object (emodin succinyl ethyl ester in a dose of 20 mg/kg·d$^{-1}$) has better effects of lowering TC (&$P<0.05$ vs. emodin group) and LDL-C (&$P<0.05$ vs. emodin group) in serum of rats than the equivalent dose of emodin (20 mg/kg·d$^{-1}$).

Example 8 Efficacy Test 4 of the Product of the Present Invention

1. Experimental Materials

Experimental cells: HepG2 cell line

Test object: Emodin succinyl ethyl ester (prepared in Examples 1-3)

2. Experimental Principle

Oleic acid is added to culture HepG2 cells to induce a hyperlipemia cell model, and then the cells are given a test drug, the effect of the test object on the lipid level of the cells is detected.

3. Experimental Methods 3.1 Cell Grouping

When the degree of cell fusion reached about 80%, except for the normal group, cells in other groups were all added with oleic acid at a dose of 200 μmol/L, and then the cells were divided into five groups: the normal group, the oleic acid-induced hyperlipemia group, low-dose emodin succinyl ethyl ester group (5 μmol/L), the medium-dose emodin succinyl ethyl ester group (10 μmol/L) and the high dose emodin succinyl ethyl ester group (20 μmol/L). 24 hours later, the levels of TC and TG were measured.

3.2 Test Methods 3.2.1 Cell Collection:

The cells were digested with 0.25% trypsin to prepare a cell suspension; the cell suspension was centrifuged at 1000 rpm for 10 minutes; the supernatant was discarded, and the cell pellet was collected, washed with PBS once or twice, and configured at 1000 rpm for 10 minutes; the supernatant was discarded, and the cell pellet was collected.

3.2.2 Cell Disruption:

200 μl of 2% TritonX-100 was added for lysis for 30 minutes.

3.2.3 Determination Method

First, the protein concentration of the sample was determined using the Beyotime kit. Then, 250 μl of working solution was added to a 96-well plate, 2.5 μl of distilled water was added to the blank wells, 2.5 μl of calibration solution was added to the calibration wells, 2.5 μl of sample was added to the sample wells, and they were all incubated for 10 minutes at 37° C. The OD values were measured by using a 510 nm microplate reader.

3.2.4 Calculation Formulas:

Cholesterol content=(sample OD value−blank OD value)/(calibrated OD value−blank OD value)*5.17/protein concentration of the sample to be tested Triglyceride content=(sample OD value−blank OD value)/(calibrated OD value−blank OD value)*2.26/protein concentration of the sample to be tested.

4. Experimental Data and Results 4.1 Data Processing

The analysis of variance is performed, but the homogeneity of variance test needs to be performed first according to the procedure of analysis of variance. If the variance is homogeneous, the F value is calculated, and 36F<0.05. Conclusion: There is no significant difference between the means of all the groups; F≥0.05, P≤0.05, and the statistics are made using a pairwise comparison of means between multiple experimental groups and one control group; appropriate variable conversion is performed on non-normal or heterogeneous-variance data; after the data after conversion become normal and homogeneous-variance data, the data are used for statistics; if the data after conversion still are non-normal and heterogeneous-variance data, rank sum test could be performed for statistics.

4.2 Experimental Results

The effect of emodin succinyl ethyl ester on the levels of TC and TG in oleic acid-induced hyperlipemia cells is shown in Table 8 and FIG. 11. From the results, it can be seen that the levels of TC (* P<0.001 vs. blank control group) and TG (* P<0.001 vs. blank control group) of oleic acid-induced hyperlipemia cells are significantly increased as compared with those of the blank control group, thus determining the successful establishment of the model. Emodin succinyl ethyl ester in low, medium, and high doses can significantly reduce the levels of TC (####P<0.001 vs. oleic acid group) and TG (#P<0.05 vs. oleic acid group) of oleic acid-induced hyperlipemia cells.

TABLE 8

Effect of emodin succinyl ethyl ester on the levels of TC and TG in oleic acid-induced hyperlipemia cells

| Group | TC (mmol/L) | TG (mmol/L) |
|---|---|---|
| Blank control group | 0.175 ± 0.080 | 0.125 ± 0.119 |
| Oleic acid group | 1.000 ± 0.000*** | 1.000 ± 0.000*** |
| Low-dose emodin succinyl ethyl ester group | 0.730 ± 0.168## | 0.610 ± 0.308# |
| Medium-dose emodin succinyl ethyl ester group | 0.506 ± 0.197###& | 0.487 ± 0.347# |
| High-dose emodin succinyl ethyl ester group | 0.537 ± 0.145###&& | 0.414 ± 0.209## |

Note:
Data are expressed as mean ± standard error,
***P < 0.001 vs. blank control group,
*P < 0.05 vs. oleic acid group,
P < 0.01 vs. oleic acid group,
P < 0.001 vs. oleic acid group, blank control group, n = 6; oleic acid group, n = 6; low-dose test object (emodin succinyl ethyl ester in a dose of 5 μmol/L) group, n = 6; medium-dose test object (emodin succinyl ethyl ester in a dose of 10 μmol/L) group, n = 6; high-dose test object (emodin succinyl ethyl ester in a dose of 20 μmol/L) group, n = 6.

The above are only the preferred embodiments of the present invention. It should be noted that, for those of ordinary skill in the art, without departing from the principles of the present invention, several improvements and retouches can be made, and these improvements and retouches should also be regarded as falling within the scope off the present invention.

What is claimed is:

1. An emodin succinyl ester compound, having a structure represented by Formula I:

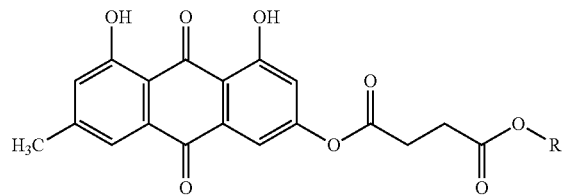

Formula I where R represents $C_{1-5}$ alkyl.

2. The emodin succinyl ester compound according to claim 1, wherein in Formula I, R represents ethyl.

3. A method for preparing the emodin succinyl ester compound according to claim 1, comprising reacting succinic anhydride and a $C_{1-5}$ alkanol; reacting the monoalkanol succinate with thionyl chloride to obtain succinate monoalkanol ester acyl chloride; and reacting the succinate monoalkanol ester acyl chloride with emodin to obtain the emodin succinyl ester compound.

4. The method according to claim 3, comprising the following steps:

(1) refluxing succinic anhydride in the presence of $C_{1-5}$ alkanol as solvent, followed by reduced-pressure distillation to remove excess alkanol, thus obtaining a monoalkanol succinate, wherein the monoalkanol succinate is subjected to the next reaction without separation;

(2) refluxing the monoalkanol succinate in the presence of thionyl chloride as solvent, followed by reduced-pressure distillation to remove excess thionyl chloride, thus obtaining succinate monoalkanol ester acyl chloride compound, wherein the compound is subjected to the next reaction without separation;

(3) placing the emodin and an alkali in a round-bottomed flask, adding the succinate monoalkanol ester acyl chloride dropwise in the presence of dichloromethane as solvent, and reacting at room temperature;
(4) extracting with a sodium hydrogen carbonate solution, combining organic phases, extracting the organic phases with saturated brine, combining organic phases, drying with anhydrous sodium sulfate, filtering, and concentrating under reduced pressure to obtain a crude product; and
(5) chromatographing the crude product on a silica gel column and eluting with a dichloromethane-methanol mixed solution to obtain the emodin succinyl ester.

5. The method according to claim 4, comprising the following steps when R represents ethyl:
(1) refluxing succinic anhydride in the presence of ethyl alcohol as solvent, followed by reduced-pressure distillation to remove excess ethyl alcohol, thus obtaining monoethyl succinate, wherein the monoethyl succinate is subjected to the next reaction without separation;
(2) refluxing the monoethyl succinate in the presence of thionyl chloride as solvent, followed by reduced-pressure distillation to remove excess thionyl chloride, thus obtaining succinate monoethyl ester acyl chloride, wherein the succinate monoethyl ester acyl chloride is subjected to the next reaction without separation;
(3) placing the emodin and an alkali in a round-bottomed flask, adding the succinate monoethyl ester acyl chloride dropwise in the presence of a solvent, dichloromethane, and reacting at room temperature;
(4) extracting with a sodium hydrogen carbonate solution, combining organic phases, extracting the organic phases with saturated brine, combining organic phases, drying with anhydrous sodium sulfate, filtering, and concentrating under reduced pressure to obtain a crude product; and
(5) chromatographing the crude product on a silica gel column and eluting with a dichloromethane-methanol mixed solution to obtain the emodin succinyl ethyl ester.

6. The method according to claim 4, wherein the alkali in step (3) is selected from weak alkalis.

7. The method according to claim 5, wherein, in step (1), the time of heating reflux is 3-10 hours, and the ratio (g:ml) of the mass of succinic anhydride to the volume of ethanol is 1:10; in step (2), the time of heating reflux is 1-10 hours, and the mass ratio of monoethyl succinate to thionyl chloride is 1:1-1:10, in step (3), the alkali is pyridine, triethylamine, or ammonia, and the mass ratio of emodin to succinate monoethyl ester acyl chloride is 1:0.5-1; in step (5), in the dichloromethane-methanol mixed solution, the volume ratio of dichloromethane to methanol is 100:1-100:4.

8. A composition comprising the emodin succinyl ester compound according to claim 1 for use in a pharmaceutical composition for diabetic wound healing.

9. A pharmaceutical composition, comprising the emodin succinyl ester compound according to claim 1, and optionally one or more excipients, wherein the pharmaceutical composition is selected from cream, oil, patch, powder, spray, sustained release agent preparation, capsule, tablet, granule, or injection.

10. An oily preparation, comprising the emodin succinyl ester compound according to claim 1 and a vegetable oil.

11. A method for preparing the oily preparation according to claim 10, comprising the following steps:
(1) heating vegetable oil to a browned state for sterilization, resting at room temperature, and cooling for later use;
(2) weighing the emodin succinyl ester compound according to claim 1 under an aseptic condition and dissolving the compound in the vegetable oil after sterilization in step (1); wherein, the ratio (mg:ml) of the mass of the succinyl ester compound to the volume of the vegetable oil is 1-5:1;
(3) carrying out ultrasonic vibration on the vegetable oil which contains the emodin succinyl ethyl ester, so that the emodin succinyl ethyl ester is fully dissolved to form a uniform oily preparation; and
(4) diluting the oily preparation obtained in step (3) with sterile water, sub-packaging under an aseptic condition, sealing, and storing at room temperature for later use; wherein, in the oily preparation diluted with sterile water, the concentration of the emodin succinyl ester compound is 50-150 µg/mL.

12. The emodin succinyl ester compound according to claim 1 for use in a pharmaceutical composition for lowering blood lipids and/or for treating fatty liver.

13. The emodin succinyl ester compound according to claim 12 for use in the lipid-lowering pharmaceutical composition, wherein the lipid-lowering pharmaceutical composition reduces total cholesterol (TC), low-density lipoprotein (LDL-C) in a serum, and a TC and triglycerides (TG) in a liver.

14. The method according to claim 7, wherein, in step (1), the time of heating reflux is 4 hours, and the ratio (g:ml) of the mass of succinic anhydride to the volume of ethanol is 1:4; in step (2), the time of heating reflux is 2 hours, and the mass ratio of monoethyl succinate to thionyl chloride is 1:4; in step (3), the alkali is pyridine, and the mass ratio of emodin to succinate monoethyl ester acyl chloride is 1:0.7; in step (5), in the dichloromethane-methanol mixed solution, the volume ratio of dichloromethane to methanol is 100:1.

15. A method for preparing the oily preparation according to claim 11, comprising the following steps:
(1) heating vegetable oil to a browned state for sterilization, resting at room temperature, and cooling for later use;
(2) weighing the emodin succinyl ester compound according to claim 1 under an aseptic condition and dissolving in the vegetable oil after sterilization in step (1); wherein, the ratio (mg:ml) of the mass of the succinyl ester compound to the volume of the vegetable oil is 4:1;
(3) carrying out ultrasonic vibration so that the emodin succinyl ethyl ester is fully dissolved to form a uniform oily preparation; and
(4) diluting the oily preparation obtained in step (3) with sterile water, sub-packaging under an aseptic condition, sealing, and storing at room temperature for later use; wherein, in the oily preparation diluted with sterile water, the concentration of the emodin succinyl ester compound is 100 µg/mL.

\* \* \* \* \*